United States Patent [19]

Cavanak

[11] Patent Number: 4,654,345

[45] Date of Patent: Mar. 31, 1987

[54] OCCULAR FORMULATION COMPRISING BROMOCRIPTINE

[75] Inventor: Thomas Cavanak, Biel-Benken, Switzerland

[73] Assignee: Sandoz Ltd., Basel, Switzerland

[21] Appl. No.: 789,251

[22] Filed: Oct. 18, 1985

[30] Foreign Application Priority Data

Oct. 24, 1984 [GB] United Kingdom ................. 8426922

[51] Int. Cl.$^4$ .................... A61K 31/50; A61K 31/495
[52] U.S. Cl. ...................................... 514/250; 514/913
[58] Field of Search ................................ 514/250, 913

[56] References Cited

U.S. PATENT DOCUMENTS

| 4,091,099 | 5/1978 | Fehr et al. | 514/250 |
|---|---|---|---|
| 4,219,555 | 8/1980 | Rucman et al. | 514/250 |
| 4,462,983 | 7/1984 | Azria et al. | 514/250 |
| 4,486,416 | 12/1984 | Soll et al. | 424/180 |
| 4,547,500 | 10/1985 | Bolliger et al. | 514/250 |

FOREIGN PATENT DOCUMENTS

| 2030139 | 4/1980 | United Kingdom | 514/250 |
|---|---|---|---|
| 2058746 | 4/1981 | United Kingdom | 514/250 |

OTHER PUBLICATIONS

The Theory and Practice of Industrial Pharmacy-2nd ed. pp. 521-524 (1976)—Lea & Febiger-Philadelphia, Pa.
Chem. Abst. 69:61505q (1968)—Marso.
Chem. Abst. 99:980p (1983)—Nistico et al.
Chem. Abst. 100:114,972g (1984)—Mekki et al.

Primary Examiner—Douglas W. Robinson
Attorney, Agent, or Firm—Gerald D. Sharkin; Robert S. Honor; Walter F. Jewell

[57] ABSTRACT

Lyophylisates comprising bromocriptine or an acid addition salt thereof capable of reconstitution in an isotonic vehicle to provide a stable formulation for occular instillation, useful e.g. in the treatment of glaucoma. Typical lyophylisates in accordance with the invention comprise: a lyophylisable acid, e.g. methane sulfonic acid, an acid addition salt of bromocriptine with said acid, e.g. bromocriptine mesylate, benzalkonium chloride and a lyophylisate matrix material.

22 Claims, No Drawings

OCCULAR FORMULATION COMPRISING BROMOCRIPTINE

The present invention relates to novel galenic formulations, in particular novel galenic formulations comprising bromocriptine as active ingredient and suitable for occular instillation, e.g. in the treatment of glaucoma.

Bromocriptine (also known as 2-bromo-α-ergokryptin and commercially available as the mesylate salt under the Trade Mark Parlodel or Pravidel—c.f. Merck Index, Tenth Edition, 1386) is a known dopaminergic drug. More recently Bromocriptine has been shown to be of potential utility in the treatment of glaucoma as evidenced by its ability to ellicit a dose and time related reduction of intraocular pressure on local instillation into the rabbit eye at concentrations of from 0.001 to 1.0% [c.f. Potter et al., Fed. Proc. 41 (4) 1057, Abstract 4599 (1982) and Curr. Eye Res. 2 (5), 281–288 (1981–82)], as well as to effect significant reduction in intraocular pressure without change in pupil diameter on oral administration to human volunteers at dosages of 1.25 mg [Mekki et al., Lancet 1983/I, 1250–1251].

Despite this potential utility however, use of bromocriptine in treating glaucoma has been severely impeded by the absence of any dosage form suitable for practical use in this indication. Thus oral administration will result in bromocriptine exerting its other pharmaceutical effects, e.g. general dopaminergic and prolactin secretion inhibiting activity. This would be clearly undesirable in subjects requiring treatment for glaucoma alone.

An evident choice for administration in glaucoma is a topical form for direct occular instillation. However for practical clinical application such a form demands that the necessary criteria of stability, patient compliance and tolerability as well as general patient usability be met. In the case of bromocriptine the development of forms suitable for direct occular instillation meeting these criteria is hindered by the known high insolubility of the drug and of its acid addition salts. In particular bromocriptine, e.g. in mesylate form, has been found to be insufficiently soluble in media conventionally employed for occular instillation, e.g. employed in eye drop formulation, to permit development of a practical delivery system. Thus in conventional media bromocriptine in free or acid addition salt form rapidly precipitates out, so that the intended eye drop formulation must be made up on the spot and instilled immediately into the eye.

This problem is alluded to in the work of Potter et al. (loc. cit.), carried out using bromocriptine mesylate in 5% aqueous glucose. Rapid instillation was essential in order to achieve effectiveness. And in a subsequent report employing a bromocriptine eye-drop delivery system, comprising a thiomersal/polyvinylpyrrolidone/methanesulphonic acid/10% NaCl vehicle (Lancet, Feb. 4, 1984, 287–288) the same author draws specific attention to unsatisfactory patient tolerance encountered.

Clearly such systems would be entirely unsuitable for regular clinical therapy or for self-application by the patient. Development of a delivery system permitting storage over longer periods of time and permitting simple and convenient use and administration as well as acceptable patient compliance and tolerability is critical to the practical therapeutic application of bromocriptine in the treatment of glaucoma. The absence of applicable conventional systems has necessitated investigation of novel and inovative approaches to the problem.

In accordance with the present invention it has now suprisingly been found that employing benzalkonium chloride as preserving agent in lyophylised preparations of bromocriptine, it is possible to obtain lyophylisates which on reconstitution (e.g. dissolution) in isotonic media provide formulations which are eminently suitable for occular instillation, i.e. which are well tolerated on application to the eye and which are surprisingly stable over prolonged periods, e.g. over periods of several days or more, at normal temperature.

The present invention accordingly provides a bromocriptine delivery system (i.e. comprising lyophylisate and and isotonic vehicle) which is properly suited for occular instillation and which can itself be stored over long periods of time, e.g. over periods of months or years, thus adequately allowing for storage and transport, and which can be readily made up into the final form for occular instillation (by reconstitution of the lyophylisate with the isotonic vehicle) either by the physician or the patient. Moreover since the formulations obtained on reconstitution are themselves stable, e.g. as described above, the system of the invention also permits ready instillation without need for special administrative technique (e.g. in relation to rapidity of instillation), with consequential superiority of drug availability and effectiveness. The lyophylisates of the invention and the formulations directly preparable from them thus meet the problems, in particular of patient compliance, tolerability and usability previously encountered.

In its broadest aspect the present invention accordingly provides:

A lyophylisate comprising: (i) bromocriptine or an acid addition salt thereof as active ingredient, said lyophilisate being capable of reconstitution in an isotonic vehicle to provide a stable formulation suitable for occular instillation, e.g. in the treatment of glaucoma.

It will of course be appreciated that the requirement that formulations obtained on reconstitution of lyophylisates of the invention be suitable for occular instillation requires that individual lyophylisate ingredients [e.g. where an acid addition salt form of bromocriptine is employed as (i), the particular salt form, as well as other components, e.g. components (iii) and (iv) hereinafter described], as well the vehicle used for reconstitution be themselves acceptable for occular instillation following reconstitution, i.e. are acceptable for occular instillation at final dosage concentrations achieved on reconstitution. Bromocriptine acid addition salts meeting this criterium will be any of those generally known in the art as suitable for use in relation to drugs which are to be applied topically to the eye including e.g. the mesylate. Such salt forms generally have levels of activity and bioavailability of the same or similar order to those of the free compound.

The formulations obtained on reconstitution of the lyophilisates of the invention are stable, i.e. storable at ambient temperatures over periods in excess of 5 or 7 days and up to e.g. 10 days, without significant evidence of deterioration, e.g. discoloration or precipitation, in particular without significant loss of active ingredient, e.g. through precipitation or decomposition. Thus formulations in accordance with the invention and comprising benzalkonium chloride as preserving agent are storable at 5° C. for periods of 7 and 14 days, up to or in excess of 21 days, or at ambient temperature for periods of 5 and 7 days, up to or in excess of 10 days without significant evidence of observable deterioration, e.g. discoloration or of precipitation, and, in particular without significant determinable loss of active ingredient, e.g. bromocriptine mesylate, e.g. through precipitation or decomposition, any such loss remaining within the limits of acceptability, e.g. being of the order of 10% or less. This may be shown to be in contrast with equivalent formulations obtained on reconstitution of lyophylisates comprising alternative preserving agents, e.g. thiomersal, but otherwise equivalent to lyophilisates of the invention.

Formulations obtained on reconstitution of lyophylisates in accordance with the invention and comprising benzalkonium chloride as preserving agent may also be shown to possess improved patient complience, and in particular markedly improved tolerability following occular instillation, as compared with formulations obtained on reconstitution of lyophylisates comprising other preserving agents, e.g. thiomersal, as evidenced e.g. by the results of acute eye irritation tests in animals or by observed or patient-reported occular tolerability in clinical trials.

In accordance with the foregoing the present invention provides in a more specific aspect:

A lyophylisate as hereinbefore defined comprising (ii) benzalkonium chloride as preserving agent; as well as:

A lyophylisate comprising (i) bromocriptine or an acid addition salt thereof as active ingredient, and (ii) benzalkonium chloride as preserving agent, said lyophylisate being capable of reconstitution in an isotonic vehicle to provide a formulation suitable for occular instillation, e.g. in the treatment of glaucoma.

In the lyophylisates of the invention (i) is preferably bromocriptine mesylate. Preferred lyophylisates in accordance with the invention comprise benzalkonium chloride as sole preserving agent.

[Benzalkonium chloride is the name commonly employed for a known mixture of quaternary ammonium salts typically of the generalised formula $C_6H_5$—$CH_2$—$NR(CH_3)_2.Cl$, wherein $R=C_{8-18}$alkyl—c.f. Fiedler-Lexikon der Hilfsstoffe, 2nd. Edition, Vol I, p. 169].

Especially preferred lyophylisates in accordance with the invention comprise: (iii) a lyophylisable acid, (i) an acid addition salt of bromocriptine with said acid, and (iv) a lyophylisate matrix material [whereby said components (i), (iii) and (iv) must perforce meet the above discussed criterium of suitability for occular instillation].

Most preferably component (iii) in the lyophylisates of the invention is methane sulphonic acid, whereby (i) is bromocriptine mesylate.

Preferred components (iv) are in particular polymeric matrix materials such as polyvinyl pyrrolidones. Polyvinyl pyrrolidones suitable for use as the matrix material are known and are commercially available for galenic application, e.g. under the Trade Mark "Kollidon'—c.f. Fiedler-Lexikon der Hilfsstoffe, 2nd. Edition, Vol I, pp. 526 and 527 and Vol. II, pp. 748–750. A preferred polyvinyl pyrrolidone for use in the lyophylisates of the present invention is the product "Kollidon" 17 PF available from the company BASF AG, 6700 Ludwigshafen/RG, W. Germany.

Components (i) and (ii) are preferably present in the lyophylisates of the invention in a ratio of about 1:0.1 to 2.0, more preferably about 1:0.5 to 1.5, most preferably about 1:1 p.p.w. based on the amount of free bromocriptine in (i). Acid (iii) is suitably present in an amount such that the formulation obtained on reconstitution has a pH of from about 3.5 to about 4.5, preferably about 4.0.

Components (i) and (iii) are suitably present in a ratio of about 1:0.1 to 1.0, preferably about 1:0.1 to 0.5, more preferably about 1:0.3 p.p.w., based on the amount of free bromocriptine in (i). Components (i) and (iv) are suitably present in a ratio of about 1:25 to 500, preferably about 1:50 to 200, more preferably about 1:100 p.p.w., based on the amount of free bromocriptine in (i).

The lyophylisates of the invention suitably comprise from about 0.1 to about 5.0%, preferably from about 0.5 to about 2.0%, especially about 1.0% by weight free bromocriptine or an equivalent amount of an acid addition salt thereof.

For the purpose of optical instillation, the lyophylisates of the invention are suitably put up in fixed unit form, i.e. in the form of discrete portions each comprising a predetermined quantity of lyophylisate, and hence predetermined quantity of active ingredient, e.g. bromocriptine mesylate. Each fixed unit will be intended for reconstitution employing a predetermined volume of isotonic vehicle, thus providing a formulation comprising active ingredient, e.g. bromocriptine mesylate, at a predetermined concentration, for optical instillation.

Suitably each fixed unit will comprise from about 1.0 to about 100 mg lyophylisate, e.g. for reconstitution in an isotonic vehicle in a ratio of e.g. about 1 mg lyophylisate: about 0.05 to about 0.01 ml vehicle, preferably in a ratio of about 1 mg lyophylisate to about 0.04 or more preferably 0.02 ml. Thus an appropriate fixed unit may comprise 100 mg lyophylisate for reconstitution in 4 or 2 ml vehicle, or 50 mg for reconstitution in 2 or 1 ml vehicle. Where the lyophylisate comprises e.g. ca. 1% by weight free bromocriptine or equivalent amount of an acid addition salt thereof the obtained formulation for instillation will comprise (the equivalent of) ca. 0.025% or ca. 0.05% free bromocriptine.

Suitably the reconstituted formulation will be administered in drop form, e.g. in the form of a single drop treatment, with each drop comprising e.g. ca. 0.05 ml, e.g. from ca. 0.02 to ca. 0.08 ml. Thus where the formulation obtained on reconstitution has a volume of e.g. 1.0 ml, this will be appropriate for e.g. ca. 20 individual treatments. Where the reconstituted formulation is to be used by a single subject, e.g. for a plurality of treatments over a period of days, it is crucial that the formulation remain stable throughout the treatment period, and in this context, the significance of the present invention in terms of stability of the reconstituted formulations will be especially apparent.

Such fixed unit forms as aforesaid may comprise, e.g. the required quantitiy of lyophylisate contained in a single ampoule or in a separate chamber of a twin-chambered, occular instillation device, e.g. as hereinafter described.

The lyophylisates of the invention may be prepared in accordance with standard lyophylisation techniques known in the art, e.g. by bringing a component (i) as hereinbefore defined and a component (ii) as hereinbefore defined, suitably together with a component (iii) as hereinbefore defined and a component (iv) as hereinbefore defined, into intimate solution or suspension in an aqueous medium, e.g. in pharmaceutical grade water, and lyophylising the obtained solution or suspension.

For the purposes of instillation the lyophylisates of the invention are reconstituted in an isotonic vehicle, e.g. isotonic solution. In practice therefore, the lyophylisates of the invention are suitably provided to the user, i.e. the person who is to effect instillation, e.g. the patient, together with the isotonic vehicle with which the lyophylisate is to be reconstituted.

Accordingly in a further embodiment the present invention also provides a kit, pack or dispenser device containing or comprising (a) a lyophylisate in accordance with the present invention and (b) an isotonic vehicle suitable for occular instillation, components (a) and (b) being contained in said kit, pack or dispenser device apart.

The vehicle (b) may comprise e.g. an isotonic sugar, e.g. glucose solution. Preferably the vehicle (b) comprises an isotonic salt solution. Preferably it comprises an isotonic sodium chloride solution.

Preferably the lyophylisate (a) and vehicle (b) are both present in said kit, pack or dispenser device in fixed unit form, the quantity of (b) comprising each fixed unit thereof being sufficient to reconstitute a fixed unit of (i). Suitably the amounts/relative proportions of (a) and (b) will be as hereinbefore described.

Suitable kits, packs and dispenser devices as aforesaid will comprise e.g. components (a) and (b) in separate containers. Alternatively components (a) and (b) may be held in separate compartments or chambers of a single container. Preferably said kit, pack or dispenser device will also be provided with means to facilitate the bringing together of said lyophylisate (a) and said vehicle (b), e.g. where (a) and (b) are held in separate containers, with a pipette or like device. Where (a) and (b) are held in separate compartments or chambers of a single container, the latter may for example take the form of the barrel of a twin-chambered eyedropper device, analogous to the barrels of twin-chambered syringes, with (a) and (b) kept separate prior to use and with means provided such that (a) and (b) may readily be brought together and shaken to effect reconstitution. Such containers are well known in the art. Commonly the barrel is supplied on its own and is provided with means for attaching the delivery device, i.e. an eyedropper, at one end and/or means for inserting a plunger at the other. In one particular form the barrel is divided into two chambers by a resilient, intervening wall, e.g. of rubber or plastics material, movable within the barrel. The barrel is provided with a conduit at its side, displaced from the intervening wall towards the end of the barrel which bears or will receive the dropper. On actuation of the plunger, the intervening wall is displaced to a position adjacent the conduit. In this position the conduit effects connection between the two chambers and further actuation of the plunger forces the contents of the chamber distal to the dropper-end of the barrel into the chamber proximal to the dropper-end. Further actuation of the plunger after mixing the contents from the distal chamber with the contents in the proximal chamber effects delivery via the dropper. For present purposes (a) is preferably contained in the chamber proximal to the dropper-end and (b) in the chamber distal to the dropper-end.

In addition to the foregoing the present invention also provides a preparation for occular instillation comprising a lyophylisate in accordance with the present invention reconstituted in an isotonic vehicle as hereinbefore described and defined.

The following examples are illustrative of the invention:

EXAMPLES

1. Bromocriptine lyophylisate

| | INGREDIENTS | AMOUNT |
|---|---|---|
| A | Bromocriptine mesylate | 1.806 g |
| B | Pharmaceutical grade water | ca. 2.5 liters |
| C | 10% Methanesulphonic acid | 4.8 g |
| D | Kollidon 17 PF | 150.0 g |
| $E^1$ | Benzalkonium chloride | 1.575 g* in |
| $E^2$ | Pharmaceutical grade water | 20.0 g |
| F | Pharmaceutical grade water to an end volume of | 3.0 liters |

*plus 5% excess for loss in processing

A is suspended in B with stirring. C is then added followed by D. $E^1$ is dissolved in $E^2$ with light warming and $E^1+E^2$ added to $A+B+C+D$. F is then added to the indicated end-volume, and the whole subjected to double filtration using a Millipore, 142 mm filter apparatus and a Pall Ultipore, NM 0.2 my filter, with the second filtration carried out at a pressure of 0.5 bar (bubble point=2.6 bar). The obtained filtrate is filled in 2.0 ml portions into 10 ml vials and lyophylised employing a Usifroid SMH apparatus. The vials are gassed and closed in a freeze drier. The whole procedure is carried out under appropriate sterile conditions. Each vial contains bromocriptine lyophylisate in accordance with the invention and comprising A, C, D and $E^1$ in the following amounts: (A) 1.204 mg (1.147 mg mesylate=1 mg base/amount of mesylate includes a 5% excess); (C) 0.32 mg; (D) 100 mg; ($E^1$) 1.05 mg.

2. Isotonic vehicle

As isotonic vehicle for reconstitution of the above lyophylisate there is employed a standard pharmaceutical grade isotonic NaCl solution. This is put up in fixed unit form in vials, with each vial containing a 2 or 4 ml portion.

3. Reconstitution of 1 with 2

Reconstitution of the lyophylisate 1 with vehicle 2 is effected by introduction of 2 into the vials containing 1, e.g. by means of a syringe or pipette and, if necessary, shaking. The obtained composition comprises a clear colourless solution having a pH of ca. 3.63 and a bromocriptine free base concentration of ca. 0.05% or 0.025%, and suitable for occular instillation.

4. Stability testing

Stability of lyophilisates in accordance with the invention following reconstitution is suitably performed in accordance with standard procedures, e.g. employing test compositions comprising lyophilisate 1 dissolved in 10 ml portions of isotonic vehicle as described under 2. Such compositions are found to be substantially stable, e.g. capable of storage for up to ca. 3 weeks at 5° C. and up to ca. 10 days at ambient temperature without visible deterioration or precipitation. In one such trial loss of active ingredient, e.g. through decomposition as determined by regular HPLC technique, is found to be of the order of, e.g. 10% or less after 10 days at ca. 21° C., or of the order of e.g. 5% or less after 21 days at ca. 5° C.

I claim:
1. A lyophylisate comprising
   (i) a therapeutic amount for the treatment of interocular pressure of bromocriptine or an acid addition salt thereof as active ingredient,

(ii) benzalkonium chloride as preserving agent, and
(iii) a polymeric matrix material,
wherein component (i) and component (ii) are present in a ratio of 1 to 0.1–2.0, respectively, said lyophylisate being capable of reconstitution in an isotonic vehicle to provide a stable formulation suitable for occular instillation.

2. A lyophylisate comprising
(i) bromocriptine or an acid addition salt thereof as active ingredient, and
(ii) benzalkonium chloride as preserving agent,
said lyophylisate being capable of reconstitution in an isotonic vehicle to provide a formulation suitable for occular instillation.

3. A lyophylisate according to claim 2 comprising
(ii) benzalkonium chloride as sole preserving agent.

4. A lyophylisate according to claim 2 comprising
(iii) a lyophylisable acid,
(i) an acid addition salt of bromocriptine with said acid, and
(iv) a lyophylisate polymeric matrix material.

5. A lyophylisate according to claim 2 wherein (i) is bromocriptine mesylate.

6. A lyophylisate according to claim 4 wherein (iv) comprises a polymeric matrix material.

7. A lyophylisate according to claim 6 wherein (iv) is polyvinyl pyrrolidone.

8. A lyophylisate according to claim 2 wherein (i) and (ii) are present in a ratio of about 1:0.1 to 2.0 p.p.w., based on the amount of free bromocriptine in (i).

9. A lyophylisate according to claim 8 wherein (i) and (ii) are present in a ratio of about 1:0.5 to 1.5 p.p.w., based on the amount of free bromocriptine in (i).

10. A lyophilisate according to claim 9 wherein (i) and (ii) are present in a ratio of about 1:1 p.p.w., based on the amount of free bromocriptine in (i).

11. A lyophylisate according to claim 4 wherein (i) and (iii) are present in a ratio of about 1:0.1 to 1.0 p.p.w. based on the amount of free bromocriptine in (i).

12. A lyophylisate according to claim 11 wherein (i) and (iii) are present in a ratio of about 1:0.1 to 0.5 p.p.w., based on the amount of free bromocriptine in (i).

13. A lyophylisate according to claim 12 wherein (i) and (iii) are present in a ratio of about 1:0.3 p.p.w., based on the amount of free bromocriptine in (i).

14. A lyophylisate according to claim 4 wherein (i) and (iv) are present in a ratio of about 1:25 to 500 p.p.w., based on the amount of free bromocriptine in (i).

15. A lyophylisate according to claim 14 wherein (i) and (iv) are present in a ratio of about 1:50 to 200 p.p.w., based on the amount of free bromocriptine in (i).

16. A lyophylisate according to claim 15 wherein (iii) and (iv) are present in a ratio of about 1:100 p.p.w., based on the amount of free bromocriptine in (i).

17. A lyophylisate according to claim 2 comprising from about 0.1 to about 5.0% by weight free bromocriptine or equivalent amount of an acid addition salt thereof.

18. A lyophylisate according to claim 17 comprising from about 0.5 to about 2.0% by weight free bromocriptine or equivalent amount of an acid addition salt thereof.

19. A lyophylisate according to claim 18 comprising about 1.0% by weight free bromocriptine or equivalent amount of an acid addition salt thereof.

20. A lyophylisate according to claim 2 in fixed unit form.

21. A lyophylisate according to claim 20 comprising from about 1.0 to about 100 mg lyophylisate per unit.

22. The method of treating elevated intraocular pressure comprising the ocular instillation of a lyophylisate of claim 1 or claim 3 which has been reconstituted in an isotonic vehicle in an amount sufficient to reduce the elevated intraocular pressure.

* * * * *